United States Patent
Chu et al.

(10) Patent No.: US 6,211,224 B1
(45) Date of Patent: Apr. 3, 2001

(54) ANTAGONISTS OF GONADOTROPIN RELEASING HORMONE

(75) Inventors: Lin Chu, Scotch Plains; Mark Goulet, Westfield; Thomas F. Walsh, Watchung; Matthew J. Wyvratt, Mountainside; Stephanie L. Witkin, Teaneck, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/178,688

(22) Filed: Oct. 26, 1998

Related U.S. Application Data

(60) Provisional application No. 60/063,312, filed on Oct. 28, 1997.

(51) Int. Cl.⁷ .................... A61K 31/404; C09B 209/14
(52) U.S. Cl. ................................. 514/415; 548/506
(58) Field of Search .................. 548/506; 514/415

(56) References Cited

U.S. PATENT DOCUMENTS

| | | | |
|---|---|---|---|
| 4,255,432 | 3/1981 | Kluge et al. | 514/278 |
| 4,272,533 | 6/1981 | Gadient et al. | 514/212 |
| 5,604,253 | 2/1997 | Lau et al. | 514/415 |
| 5,756,507 | 5/1998 | Goulet et al. | 514/255 |
| 5,780,437 | 7/1998 | Goulet et al. | 514/19 |
| 5,849,764 | 12/1998 | Goulet et al. | 514/337 |

FOREIGN PATENT DOCUMENTS

WO97/21707   6/1997   (WO) .

OTHER PUBLICATIONS

Drugs of the Future, vol. 13, No. 8, pp. 761–787 (1988), by A. Dutta.
Current Opinion in Obstet. & Gyno., vol. 6, pp. 262–268 (1994), by R. Loy.
TEM, vol. 3, No. 1, pp. 30–34 (1992), by R. Barbieri.
Drugs, vol. 35, pp. 63–82 (1988), by M. Filicori, et al.
Human Reproduction, vol. 11, Suppl. 3, pp. 89–101 (1996), by U. Cirkel.
Human Reproduction, vol. 11, Suppl. 1, pp. 123–132 (1996), by G. Hodgen.

*Primary Examiner*—Fiona T. Powers
(74) *Attorney, Agent, or Firm*—Soonhee Jang; Mark R. Daniel

(57) ABSTRACT

There are disclosed compounds of formula (I)

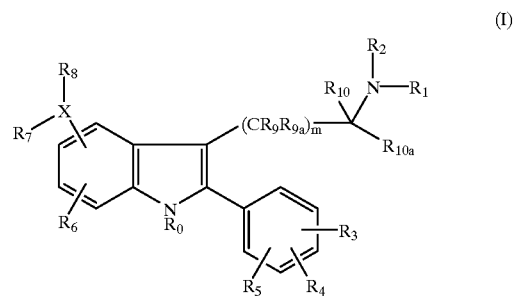

and pharmaceutically acceptable salts thereof which are useful as antagonists of GnRH and as such may be useful for the treatment of a variety of sex-hormone related and other conditions in both men and women.

19 Claims, No Drawings

ANTAGONISTS OF GONADOTROPIN RELEASING HORMONE

This application claim benefit to Provisional Application 60/063312 filed Oct. 28, 1997.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd. Additional non-peptide GnRH antagonists have been described in WO 97/21704, WO 97/21707, WO 97/21703 and WO 97/21435.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male antifertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril, Lisinopril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or episteride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula

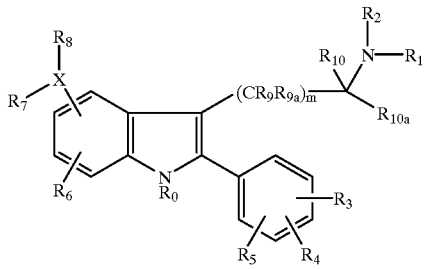

(I)

wherein
- $R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R_5$.
- $R_1$ and $R_2$ are independently hydrogen, $C_1$–$C_6$ alkyl, substituted $C_1$–$C_6$ alkyl, $C_3$–$C_7$ cycloalkyl, substituted $C_3$–$C_7$ cycloalkyl, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$, $C_3$–$C_6$ alkenyl, substituted $C_3$–$C_6$ alkenyl, $C_3$–$C_6$ alkynyl, substituted $C_3$–$C_6$ alkynyl, $C_0$–$C_5$-alkyl-S(O)$_n$-$C_0$–$C_5$ alkyl, $C_2$–$C_6$ alkyl(NR$_{11}$R$_{12}$), $C_2$–$C_6$ alkyl(OR$_{11}$), or $C_1$–$C_6$alkyl(CONR$_{11}$R$_{12}$); with the proviso that $R_{11}$ and $R_{12}$ independently or taken together are not aryl, substituted aryl, aralkyl, or substituted aralkyl; or
- $R_1$ and $R_2$ taken together form an optionally substituted non-heteroaromatic ring of 3–8 atoms containing 0,1 or 2 additional heteroatoms selected from S, O or N;
- $R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}$O(CH$_2$)$_p$-, $R_{11}$C(O)O(CH$_2$)$_p$-, $R_{11}$OC(O)(CH$_2$)$_p$-, -(CH$_2$)$_p$S(O)$_n$R$_{17}$, —(CH$_2$)$_p$C(O)N$_{11}$R$_{12}$ or halogen; wherein $R_{17}$ is hydrogen, $C_1$–$C_6$ alkyl, $C_1$–$C_3$ perfluoroalkyl, aryl or substituted aryl;
- $R_3$ and $R_4$ taken together form a carbocyclic ring of 3–7 carbon atoms or a heterocyclic ring containing 1–3 heteroatoms selected from N, O and S;
- $R_6$ is hydrogen, $C_1$–$C_6$ alkyl, substituted $C_1$–$C_6$ alkyl, aryl, substituted aryl, $C_1$–$C_3$ perfluoroalkyl, CN, NO$_2$, halogen, $R_{11}$O(CH$_2$)$_p$-, NR$_{12}$C(O)R$_{11}$, NR$_{12}$C(O)NR$_{11}$R$_{12}$ or SO$_n$R$_{11}$;
- $R_7$ is hydrogen, $C_1$–$C_6$ alkyl, or substituted $C_1$–$C_6$ alkyl, unless X is hydrogen or halogen, then $R_7$ is absent;
- $R_8$ is hydrogen, C(O)OR$_9$, C(O)NR$_{20}$R$_{21}$, N R$_{20}$R$_{21}$, C(O)R$_{11}$, NR$_{20}$C(O)R$_{11}$, NR$_{20}$C(O)N R$_{20}$R$_{21}$, NR$_{20}$S(O)$_2$R$_{11}$, NR$_{20}$S(O)$_2$NR$_{20}$R$_{21}$, OC(O)R$_{11}$, OC(O)NR$_{20}$R$_{21}$, OR$_{11}$, SO$_n$R$_{11}$, S(O)$_n$NR$_{20}$R$_{21}$, $C_1$–$C_6$ alkyl or substituted $C_1$–$C_6$ alkyl, unless X is hydrogen or halogen, then $R_8$ is absent; or
- $R_7$ and $R_8$ taken together form a carbocyclic ring of 3–7 atoms;
- $R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or
- $R_9$ and $R_{9a}$ taken together form a carbocyclic ring of 3–7 atoms or

when m≠0;
- $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or
- $R_{10}$ and $R_{10a}$ taken together form a carbocyclic ring of 3–7 atoms or

;

- $R_9$ and $R_{10}$ taken together form a carbocyclic ring of 3–7 carbon atoms or a heterocyclic ring containing one or more heteroatoms when m≠0; or
- $R_9$ and $R_2$ taken together form a heterocyclic ring containing 3–7 carbon atoms and one or more heteroatoms when m≠0; or
- $R_{10}$ and $R_2$ taken together form a heterocyclic ring containing 3–7 carbon atoms and one or more heteroatoms;
- $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{20}$ and $R_{21}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

X is hydrogen, halogen, N, O, $S(O)_n$, C(O), $(CR_{11}R_{12})_p$; $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, S(O)n, C(O), or $CR_{11}R_{12}$ only $R_7$ or $R_8$ is possible;

Z is O, S, or $NR_{11}$;

m is 0–3;

n is 0–2;

p is 0–4; and the alkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentyl, isohexyl, etc.

The term "aryl" includes phenyl and naphthyl. Preferably, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular finctionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

Scheme A

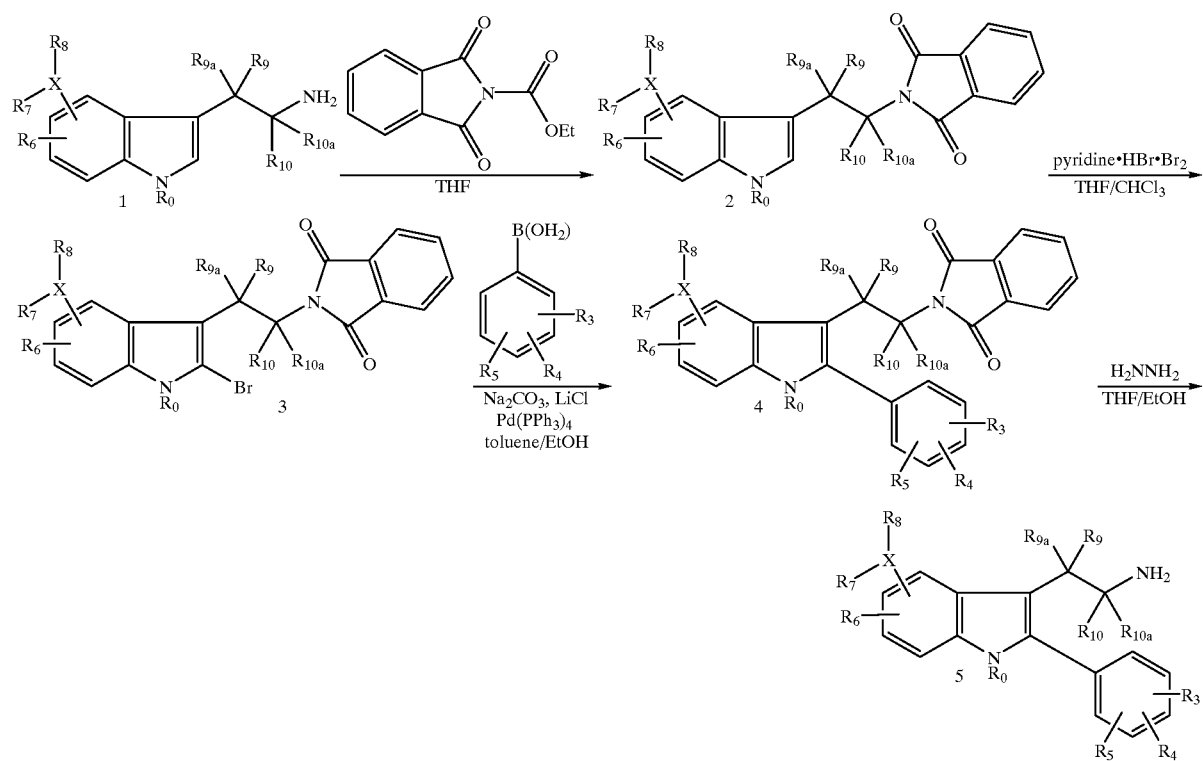

Reaction Scheme A

As shown in reaction Scheme A, treatment of tryptamine (1) with N-carboxyphthalimide in an inert organic solvent such as tetrahydrofuran at a temperature of 20–65° C., preferably 65° C., for a period of 12–48 hours gives the corresponding N-phthalimidotryptamine derivative (2). The N-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0–25° C. for a period of 30 minutes to 4 hours to provide the 2-bromotryptamine (3). Bromide (3) may be reacted with an arylboronic acid (prepared essentially as described in: Gronowitz, S.; Hornfeldt, A.-B.; Yang, Y.-H. *Chem. Scr.* 1986, 26, 311–314.) with palladium (0) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

Scheme B

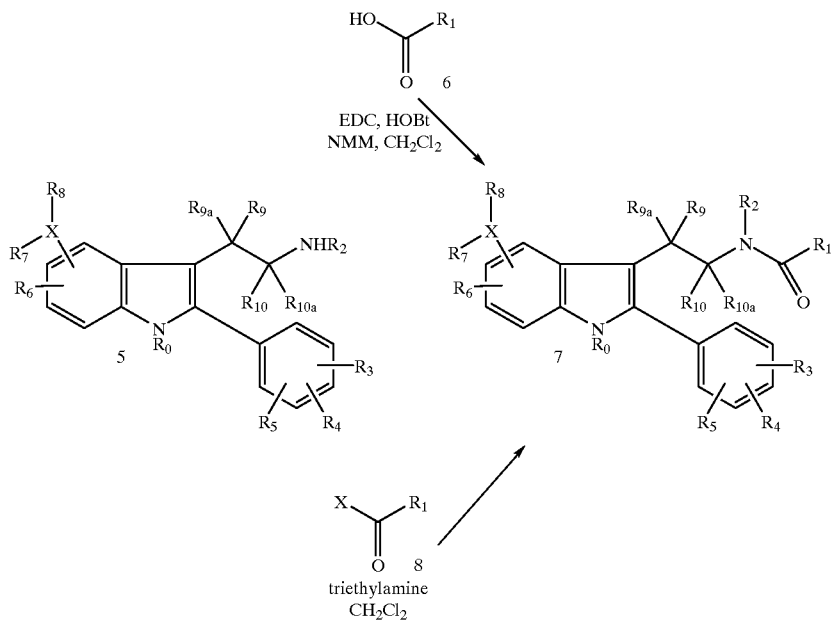

Reaction Scheme B

As shown in reaction Scheme B, the 2-aryltryptamine may be condensed with a carboxylic acid of type (6) using the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryl-tryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

-continued

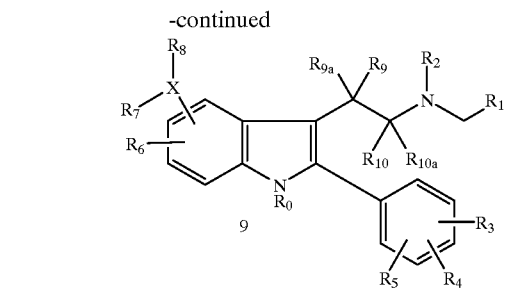

Reaction Scheme C

As shown in reaction Scheme C, the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

Scheme C

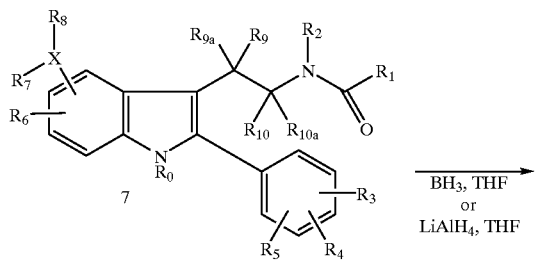

Scheme D

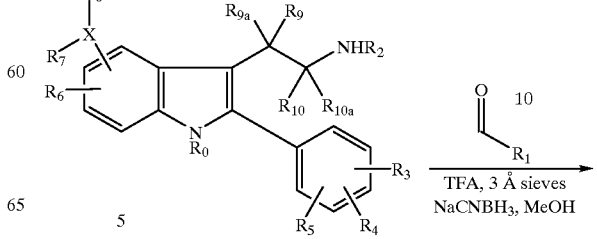

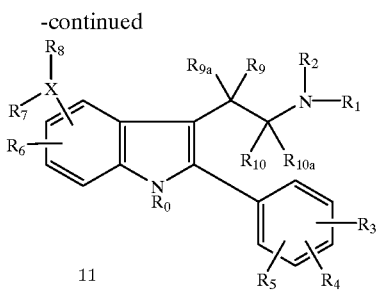

Reaction Scheme D

As shown in reaction Scheme D, the 2-aryltryptamine (5) can be modified by treatment with an aldehyde or ketone of type (10) in the presence of a weak acid such as trifluorfoacetic acid (TFA), acetic acid or the like, with or without a dessicant such as 3 Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a period of 1–12 hours to give the corresponding secondary or tertiary amine derivative (11).

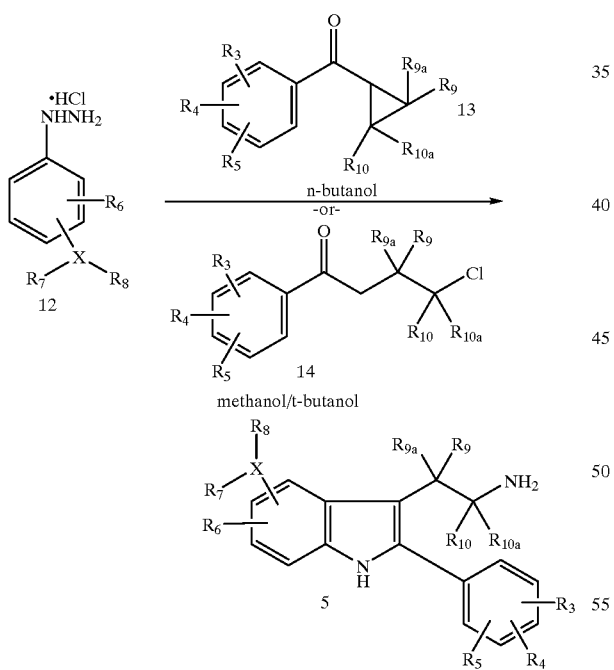

Reaction Scheme E

As shown in reaction Scheme E, treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8–24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

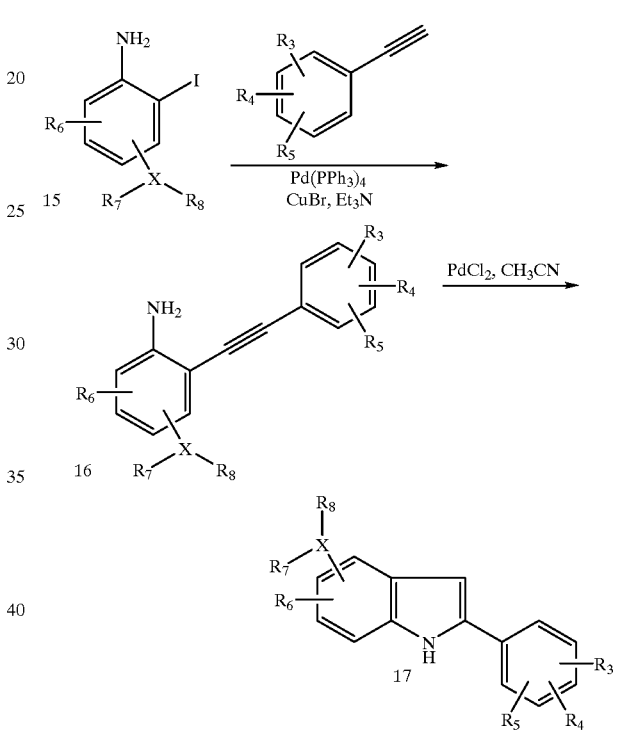

Reaction Scheme F

As shown in reaction Scheme F, iodoanilines of type (15) may be reacted with aryl acetylenes, an appropriate palladium (0) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

Scheme G

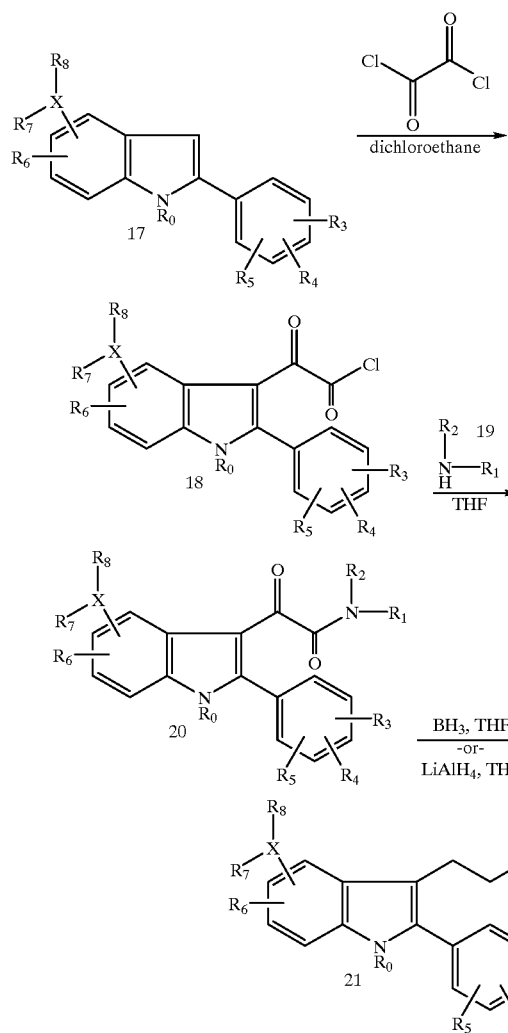

Reaction Scheme G

As shown in reaction Scheme G, treatment of 2-arylindole (17) with oxalyl chloride neat or in an inert organic solvent such as methylene chloride, chloroform, dichloroethane, tetrahydrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofuran, methylene chloride, chloroform or the like and an amine base such as triethylamine, diisopropylethylamine or pyridine at a temperature of 0° C.25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

Scheme H

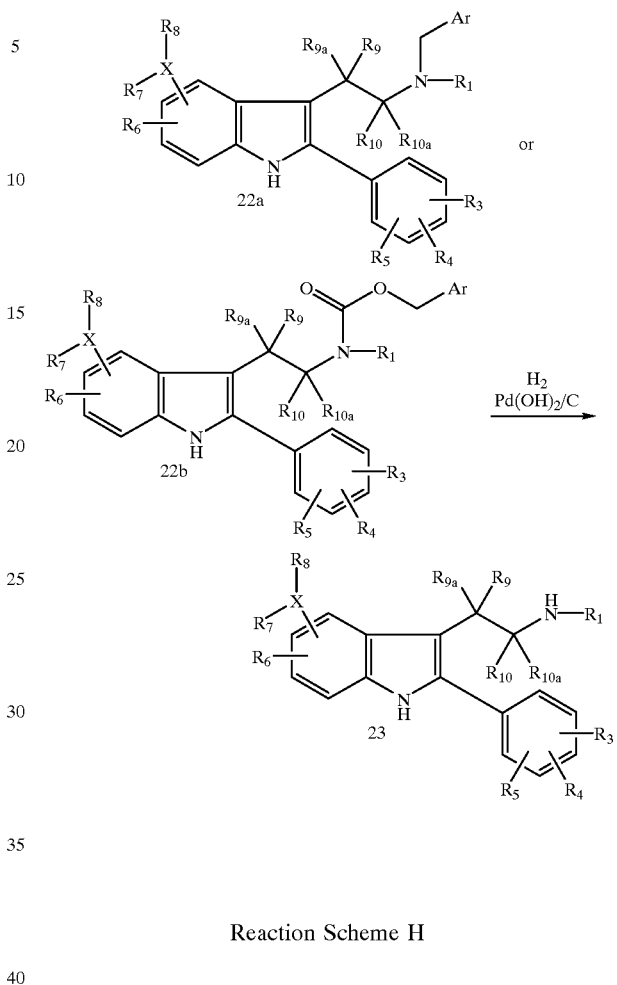

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine.

Scheme I

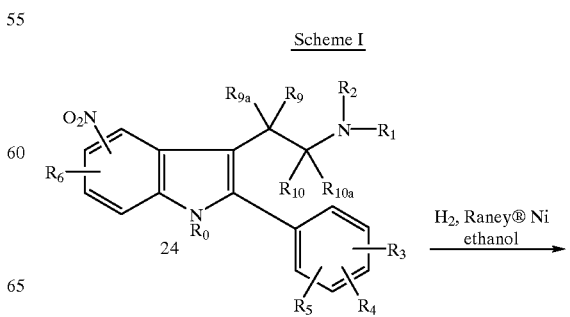

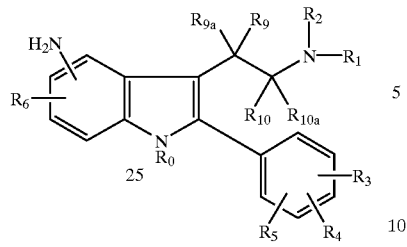

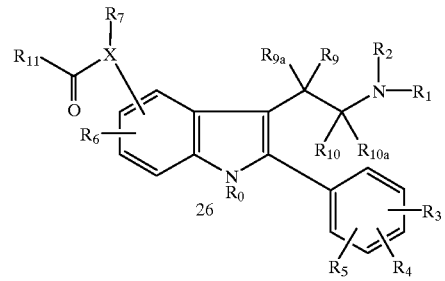

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

Reaction Scheme J

As shown in reaction Scheme J, amino- or hydroxyindole (25) may be modified by acylation under a variety of conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of aminoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

Scheme J

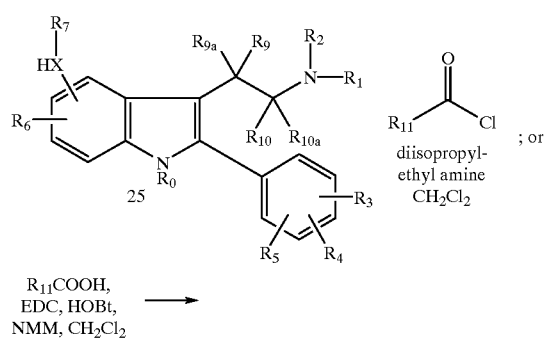

Scheme K

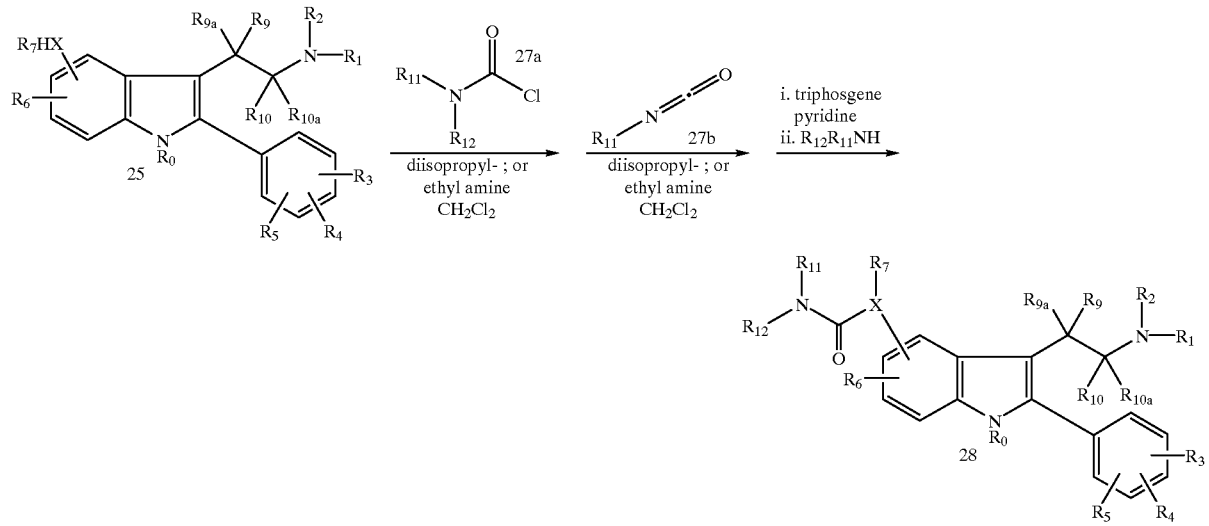

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of 0°–65° C. for a period of 1–72 hours to give (28). Compound (25) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of −20°–0° C. for a period of 20 minutes to 2 hours. After this time, the reaction mixture is treated with an appropriate mono- or disubstituted amine at −20° to 25° C. for a period of 1–5 hours to give the urea or carbamate analog (28).

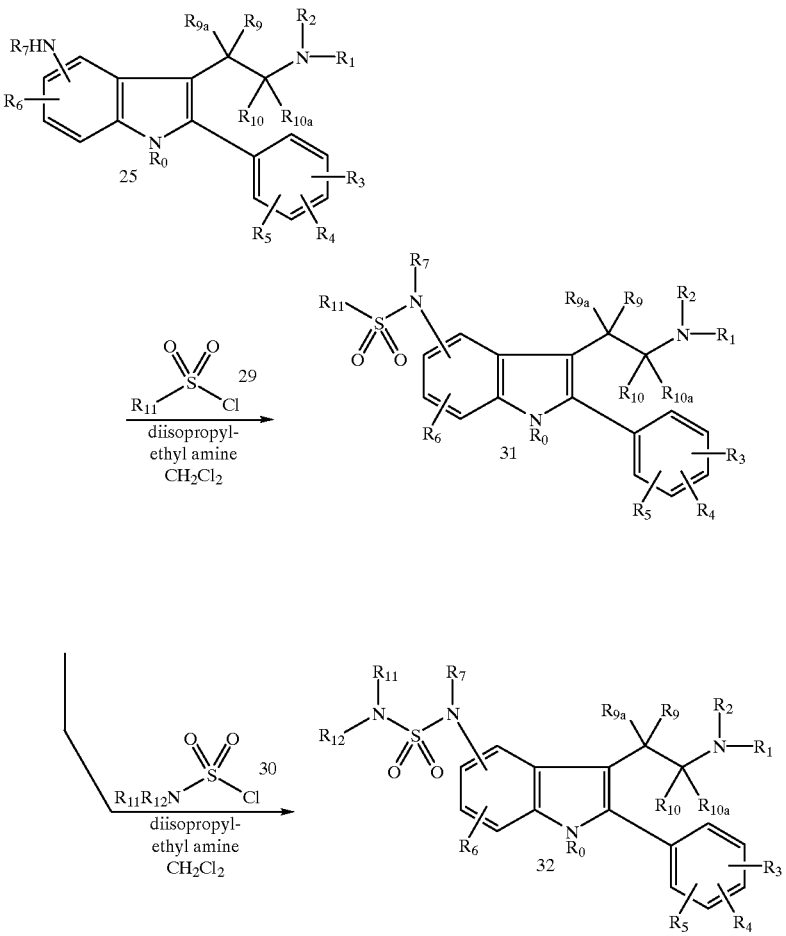

Scheme L

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichioroethane or the like at a temperature of −20°–25° C. for a period of 20 minutes to 2 hours to give the corresponding N-sulfonamide (31) or N-sulfamylamide (32) derivatives, respectively.

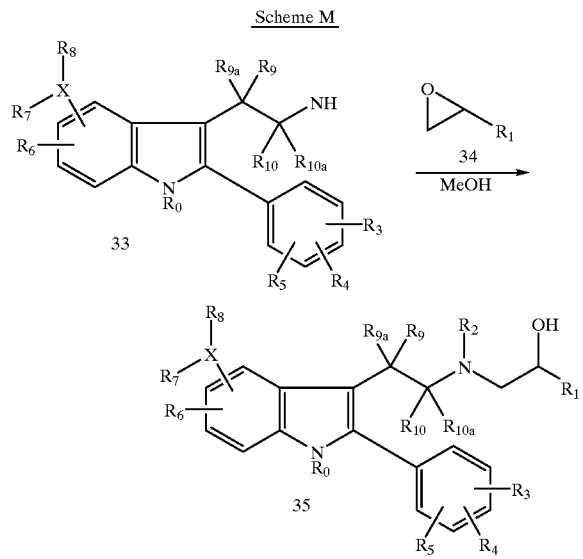

Reaction Scheme M

As shown in reaction Scheme M, the 2-aryltryptamine (33) can be modified by treatment with an epoxide such as (34) in an inert organic solvent such as methanol, ethanol, isopropanol, butanol, tert-butanol, or mixtures thereof at a temperature of 65°–110° C. for a period of 8–20 hours to give the corresponding amino-alcohol derivative (35).

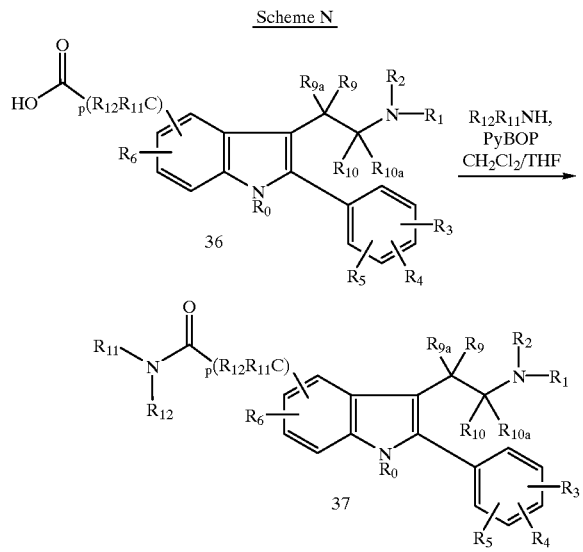

Reaction Scheme N

As shown in reaction Scheme N, amide derivatives of an acid-containing indole derivative such as (36) can be prepared by treatment with an appropriate amine ($R_{12}R_{11}NH$) and a suitable coupling agent such as benzotriazol-1-yloxyris(pyrrolidino) phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformamide, or mixtures thereof at or near room temperature for a period of 3–24 hours provides the corresponding amide derivative (37).

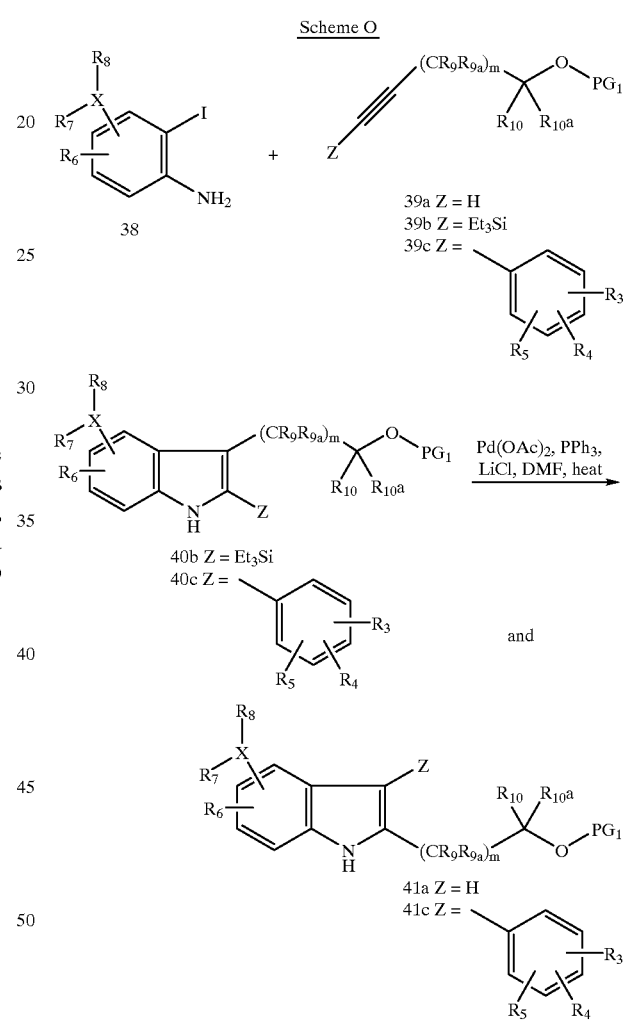

Reaction Scheme O

A preferred method for the synthesis of the substituted tryptamines described in this invention utilizes a Larock indole synthesis as a key step as shown in Scheme O. This indole synthesis involves the reaction of a suitably functionalized ortho-iodoaniline (38) with substituted acetylenes such as 39 in the presence of a base like potassium carbonate, lithium chloride, and a palladium catalyst such as palladium acetate in combination with triphenylphosphine. The reaction is conducted in an inert organic solvent such as dimethylformamide at elevated temperatures, for instance at 100° C., and the reaction is conducted for a period of 30 minutes to 24 hours. A standard workup and isolation affords the substituted isomeric indole derivatives 40 and 41, and the isomer of general formula 40 is the preferred isomer. The acetylene utilized in this reaction may be a terminal acetylene (39a) or be optionally substituted on the terminal carbon atom with a substituent Z (39b, 39c). The substituent abreviated $PG_1$ indicates an alcohol protecting group such as a benzyl ether, tert-butyl ether or the like. The nature of the Z substituent determines the distribution of the indole isomers (40 and 41) produced in the reaction. For example, if the substituent Z on the acetylene is a hydrogen atom then the isomer 41a is the major product of the reaction. When the substituent Z is chosen to be a substituted silyl group such as trimethylsilyl, triethylsilyl (as shown), or the like, then isomer 40b is formed almost exclusively. When Z is a substituted aryl group, then both isomers 40c and 41c are formed and the product mixture is separated using chromatographic or crystallization techniques to afford the individual isomers.

If the indole synthesis is conducted with a silyl-substituted acetylene 39b to produce a silyl-substituted indole 40b, then the silyl group is next converted to an aryl or substituted aryl group of general formula 40c using the reactions described later in Scheme S. The 2-arylsubstituted indole derivatives 40c formed either directly from arylacetylenes (39c) as shown in Scheme O or from silyl-substituted indoles using the method of Scheme S are then further elaborated as described below to produce the novel tryptamine derivatives described in this invention.

zene derivatives such as 42 may be commercially available or they can be readily prepared using standard methods known in organic chemistry. Reduction of the nitro group in compounds of general formula 42 using methods such as catalytic hydrogenation produces an aniline derivative such as 43. For instance when nitro compound 42 is reacted under a hydrogen atmosphere at a pressure between atmospheric pressure and 100 psig in the presence of a catalyst such as 10% palladium on powdered carbon and the reaction is conducted in an inert solvent like ethanol at temperatures between room temperature and 100° C., then the substituted aniline derivative 43 is produced usually within a period of 15 minutes to 6 hours. The generalized aniline 43 is then converted to the ortho-iodoanilines 38 by reaction with an iodinating reagent such as iodine, iodine monochloride, N-iodosuccinimide or the like. For instance, reaction of an aniline derivative like 43 with iodine monochloride in the presence of a base such as calcium carbonate and in suitable inert solvent like an alcohol (ie. methanol or ethanol) or an alcohol-water mixture at temperature between 0° C. and 50° C. affords the ortho-iodoaniline derivative 38 after reaction times between 30 minutes to 2 hours.

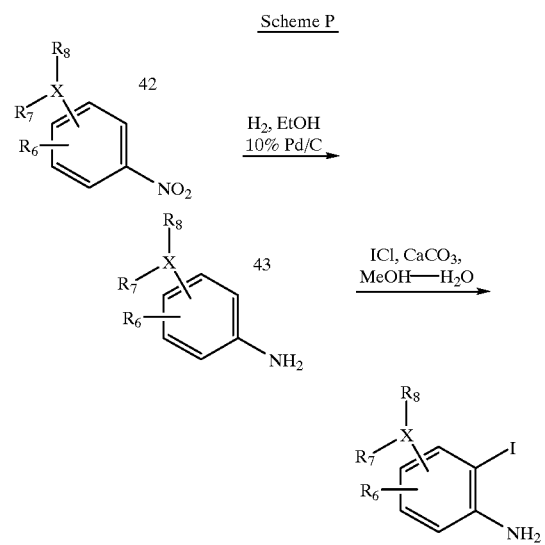

Reaction Scheme P

Scheme P illustrates the preparation of the substituted ortho-iodoaniline (38) utilized in the Larock indole synthesis described in Scheme O. The ortho-idoanilines may be prepared in several ways described in the literature of organic synthesis. One preferred method employs nitrobenzene or a substituted nitrobenzene derivative such as generalized compounds of formula 42 as the starting material. Nitroben-

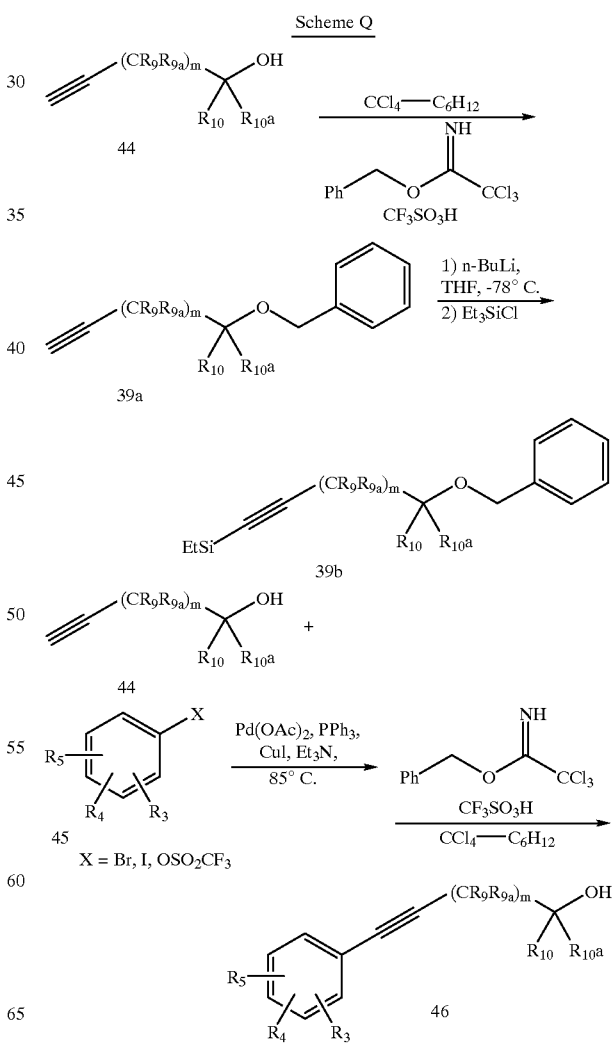

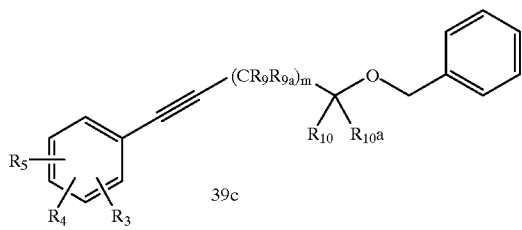

Reaction Scheme Q

Acetylenic compounds of general structure 39 are prepared using one of several methods depending upon the choice of the desired substituents. When the substituents $R_9$, $R_{9a}$, $R_{10}$ and $R_{10a}$ are selected to be hydrogen or lower alkyl groups, then compounds of formula 39 may be prepared from known acetylenic alcohols such as 3-butyn-1-ol, 4-pentyn-2-ol or similar acetylenic alcohols reported in the chemical literature. The conversion of acetylenic alcohols of general formula 44 to acetylene derivatives of general formula 39 is shown in Scheme Q. For clarity the hydroxyl protecting group ($PG_1$) illustrated in Scheme Q is exemplified as an O-benzyl ether. Thus reaction of 44 with O-benzyl-1,1,1-trichloroacetimidate in the presence of a catalytic amount of a strong acid such as trifluoromethane-sulfonic acid and in a suitable inert organic solvent like carbon tetrachloride at room temperature affords after 2 to 24 hours the protected acetylenic alcohol 39a. Compounds of formula 39a may in turn be converted to acetylenes (39b) of general formula 39 wherein Z is a trialkylsilyl group by deprotonation of the acetylene with a base such as n-butyllithium in an inert organic solvent like tetrahydrofuran followed by reaction with a trialkylsilyl chloride such as triethylchlorosilane. The deprotonation and silylation reactions are generally conducted at low temperatures, for instance between −78° C. and room temperature, and after standard workup and purification a silylacetylene of formula 39b is obtained.

As previously stated acetylenes of general formula 39c wherein Z is an aryl or substituted aryl group are also useful in the indole synthesis illustrated in Scheme O. Arylacetylenes 39c may be prepared using a coupling reaction of cuprous acetylides derived from acetylenic alcohols of formula 39a with various aryl halides or aryl triflates (45). Such coupling reactions produce aryl acetylenes of general formula 46 as shown at the bottom of Scheme Q. These reactions are generally carried out in a basic organic solvent like triethylamine at elevated temperatures, typically between 60 and 120° C., and the coupling reaction is catalyzed by copper(I) salts such as cuprous iodide and a palladium catalyst such as palladium acetate in combination with triphenylphosphine. The hydroxyl group of the arylacetylenes of general formula 46 are then usually protected with a suitable protecting group such as the O-benzyl ether group shown in Scheme Q to afford an arylacetylene (39c) of general formula 39 wherein Z is an aryl or substituted aryl group. It is also recognized that in some cases it may be preferrable to reverse the order of the steps illustrated in Scheme Q. For instance acetylenic alcohols (44) may be subjected to silylation or arylation prior to the hydroxyl group protection step.

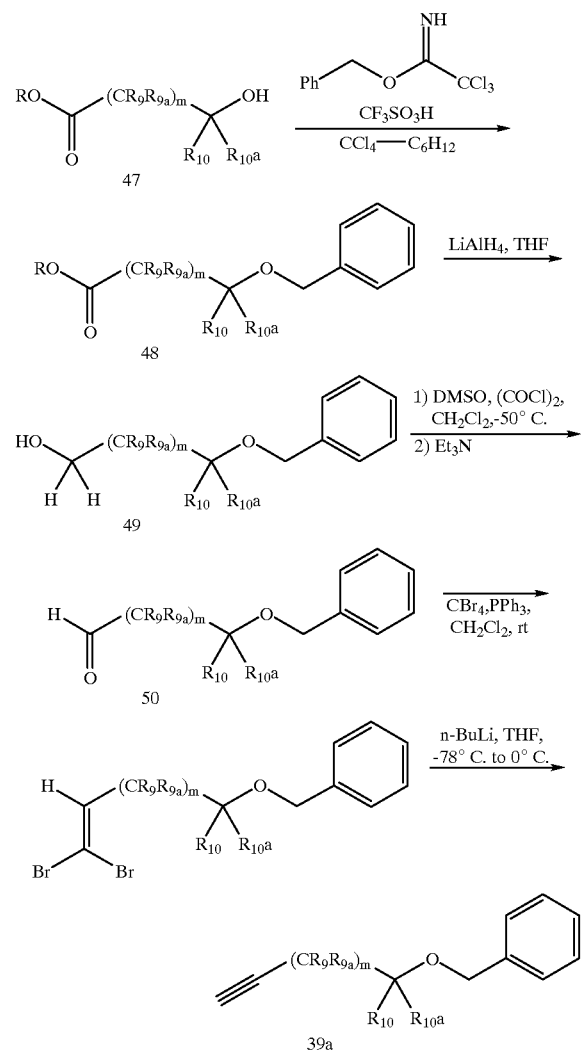

Reaction Scheme R

Another useful approach for the preparation of acetylenic compounds of general formula 39a employs an ethynylation reaction sequence of aldehydes of general formula 50 as shown in Scheme R. The aldehydes (50) used in the ethynylation sequence may be prepared using various methods known in organic synthesis starting with hydroxy-esters of general formula 47, from protected hydroxyesters of formula 48, or from alcohols related to the mono-hydroxyl protected diols of formula 49, and the choice of the prefered starting material depends upon the nature of the substituents $R_9$, $R_{9a}$, $R_{10}$, and $R_{10a}$ selected. Scheme R illustrates this strategy begining with the generalized hydroxy ester 47. Protection of the hydroxyl group of 47, for instance as the O-benzyl ether shown, affords a protected hydroxy ester of formula 48. The ester group of compounds of formula 48 is then converted to an aldehyde of formula 50 either directly using a reagent like diisobutylaluminum hydride in a solvent like toluene, or this transformation can be done in two steps. In the later case, reduction of the ester group with a reagent such as lithium aluminum hydride in tetrahydrofuran affords alcohols of formula 49 which are then subjected to reoxidation, for instance a Swern-Moffatt oxidation, to afford the desired aldehydes of formula 50.

The ethynylation of aldehydes of formula 50 is accomplished in two steps. First, aldehydes (50) are reacted with carbon tetrabromide and triphenylphosphine in an inert organic solvent like dichloromethane to produce a dibromoolefins of formula 51. Secondly, the dibromoolefins (51) are treated with two equivalents of a strong base such as n-butyllithium in tetrahydrofuran at low temperature for instance at −78° C. The strong base induces dehydrohalogenation and metal-halogen exchange to afford lithium acetylides which upon quenching and workup afford acetylenes of general formula 39a. Alternatively, the intermediate lithium acetylides formed in the reaction may be treated with a trialkylsilyl chloride such as triethylchlorosilane to afford silylacetylenes of general formula 39b.

Scheme S

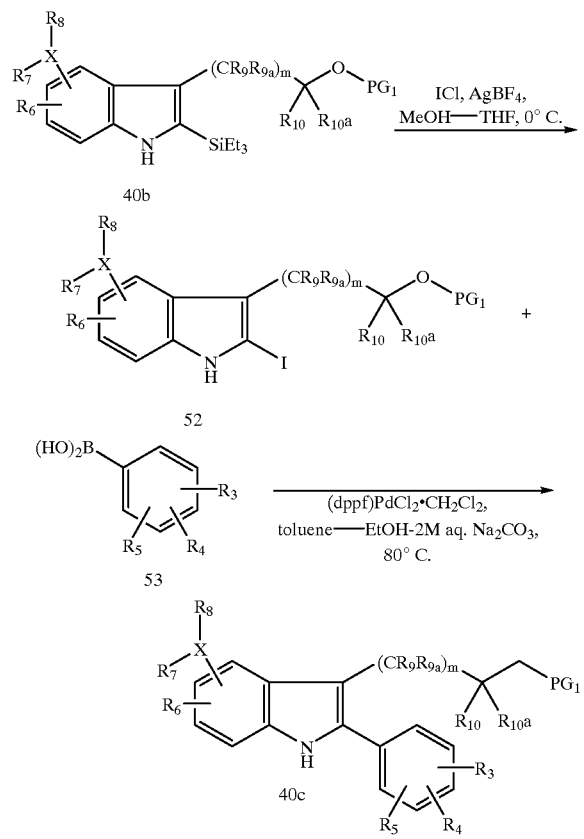

Reaction Scheme S

The conversion of 2-silyl-substituted indoles of general formula 40b to 2-aryl-substituted indoles of general formula 40c may be accomplished in two steps as shown in Scheme S. The first step is a halodesilylation reaction which converts silyl-substituted indoles of formula 40b into 2-haloindoles of general formula 52. Scheme S illustrates this process using iodine monochloride so that the product obtained is a 2-iodoindole of general formula 52. Silver tetrafluoroborate is also employed in this example to increase the reactivity of the halogenating reagent. It is possible to effect the halodesilylation reaction with other electrophilic halogenating reagents such as N-bromosuccinimide in dichloromethane which affords a 2-bromoindole derivative and both 2-bromo and 2-iodoindoles of formula 52 are useful in the subsequent step.

The second step is a palladium-catalyzed cross coupling reaction of the 2-haloindole 52 with a suitable aryl or substituted aryl organometallic reagent 53. Scheme S illustrates this process with an aryl or substituted arylboronic acid as the organometallic reagent, however other organometallic reagents known to participate in palladium-catalyzed cross-coupling reactions such as arylboronic esters or arylstannanes may also be employed. In the example shown, a 2-iodoindole of general formula 52 is coupled with a generalized boronic acid (53) using a catalyst such as [1,1'-bis(diphenylphosphino)ferrocene] dichloropalladium(II) complex with dichloromethane (shown), tetrakis (triphenylphosphine)-palladium(0) or the like. The reaction is usually conducted at temperatures between room temperature and 100° C. for instance at 80° C. This palladium catalyzed cross-coupling reaction may be effected using various combinations of palladium catalysts and solvent compositions known in organic chemistry, and the selection of the conditions is made depending upon the type of organometallic reagent (53) used and the identity of the substituent groups in the two starting materials. When the organometallic reagent is a boronic acid or boronate ester then a preferred solvent mixture consists of toluene, ethanol and an aqueous solution of a base like cesium or sodium carbonate. If instead the organometallic reagent 53 is an arylstannane, then no additional base is required, and a polar aprotic solvent such as tetrahydrofuran or dimethylformamide is employed.

Scheme T

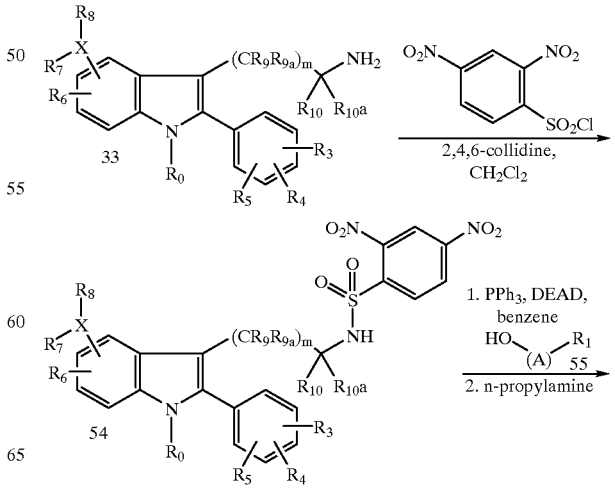

27
-continued

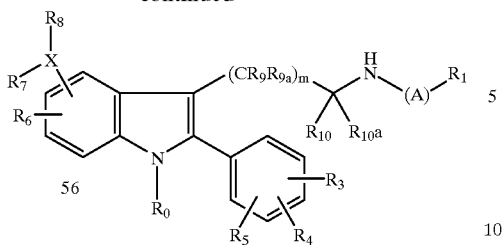

56

28
-continued

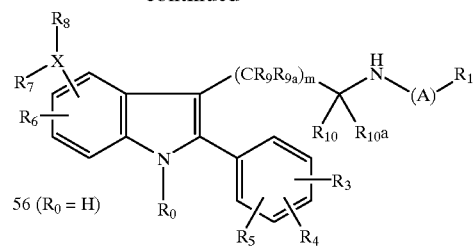

56 (R₀ = H)

Reaction Scheme T

As shown in reaction Scheme T, the tryptamine 33 can be modified using the Fukuyama modification of the Mitsunobu reaction (Fukuyama, T.; Jow, C.-K.; Cheung, M. *Tetrahedron Lett.* 1995, 36, 6373–74). The tryptamine 33 may be reacted with an arylsufonyl chloride such as 2-nitrobenzenesulfonyl chloride, 4-nitrobenzenesulfonyl chloride or 2,4-dinitrobenzenesulfonyl chloride and a hindered amine base such as 2,4,6-collidine, 2,6 lutidine or the like in an inert organic solvent such as methylene chloride to provide the corresponding sulfonamide 54. Alternatively, sulfonamide 54 can be prepared by treatment of 33 and an arylsulfonyl chloride in an inert organic solvent such as methylene chloride with excess aqueous sodium bicarbonate. The sulfonamides can be further modified by reaction with an alcohol of type 55 in the presence of triphenylphosphine and an activating agent such as diethylazodicarboxylate (DEAD), diisopropylazodicaboxylate or the like in an inert organic solvent such as benzene, toluene, tetrahydrofuran or mixtures thereof to give the dialkylsulfonamide adduct. Removal of a dinitrobenzenesulfonyl group is accomplished by treatment with a nucleophilic amine such as n-propylamine or the like in an inert organic solvent such as methylene chloride to give secondary amines of type 56. When a mono-nitrobenzenesulfonyl derivative is employed, the removal of the sulfonamide is accomplished with a more nucleophilic reagent such as thiophenol or mercaptoacetic acid in combination with lithium hydroxide in DMF.

Scheme U

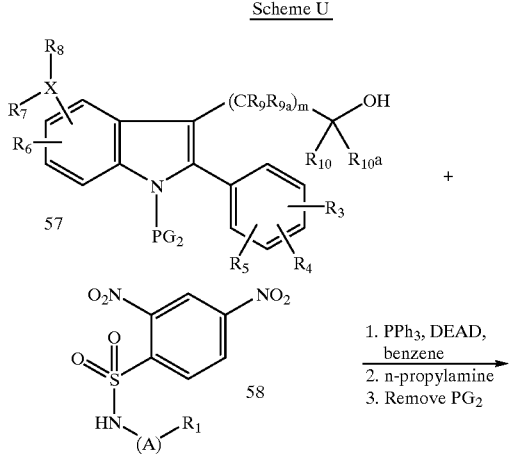

Reaction Scheme U

Reaction Scheme U illustrates a method that is complimentary to reaction Scheme T for completing the synthesis of the novel compounds of formula (I). Scheme U also employs the Fukuyama modification of the Mitsunobu reaction similar to that illustrated in reaction Scheme T. However in this instance, the alcohol partner employed is a 2-aryltryptophol of general formula 57. The 2-aryltryptophol (57) is reacted with a substituted sulfonamide of general formula 58, triphenylphosphine and diethylazodicarboxylate in a suitable inert organic solvent such as benzene, tetrahydrofuran, 1,4-dioxane or the like. The reaction is generally conducted at room temperature for a period of 2 to 24 hours, typically overnight or for about 12–16 hours. The product is an N,N-disubstituted sulfonamide which is then separately subjected to reaction with a base such as n-propylamine which removes the sulfonamide substituent and furnishes a secondary amine related to formula 57. The sulfonamides of formula 58 employed are readily obtained from a primary amine and either 2-nitrobenzene-sulfonyl chloride, 4-nitrobenzenesulfonyl chloride or 2,4-dinitrobenzene-sulfonyl chloride (as shown) in the presence of a hindered amine base such as 2,4,6-collidine, 2,6-lutidine or the like in an inert organic solvent such as methylene chloride. The final stage of the synthesis requires removal of the protecting group on the indole nitrogen atom (PG2) which produces a compound of general formula 56 wherein R0 is a hydrogen atom. It will be recognized by individuals skilled in the art of organic synthesis that a preference for utilizing either the synthetic sequences outlined in reaction Schemes T or U will be determined by the substituents selected to be present in the compounds of formula (I).

Scheme V

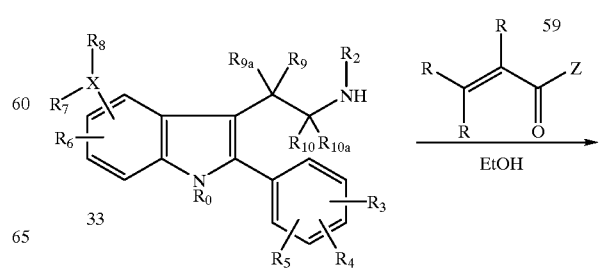

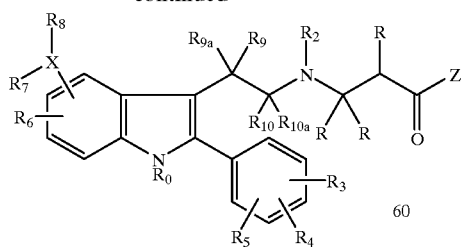

60

Reaction Scheme V

As shown in Reaction Scheme V, 2-aryltryptamine 33 can be modified by treatment with an appropriate alpha, beta-unsaturated carbonyl containing compound such as 59. Compound 59 can be variously substituted with (R) and, depending on the nature of "Z", may be either a ketone, ester or amide. The reaction of 33 and 59 proceeds in an inert organic solvent such as ethanol at a temperature of 25° to 70° C. for a period of 1 to 24 hours to provide adduct 60.

The compounds of the present invention are useful in the treatment of various sex-hormone related conditions in men and women. This utility is manifested in their ability to act as antagonists of the neuropeptide hormone GnRH as demonstrated by activity in the following in vitro assays.

Human GnRH Receptor Binding Assay

Crude membranes prepared from CHO cells expressing human GnRH receptors were the sources for GnRH receptor. [$^{125}$I]Buserelin (a peptidyl GnRH analog) was used as the radiolabelled ligand. The binding activity was determined as an $IC_{50}$ which is the antagonist concentration required to inhibit the specific binding of [$^{125}$I]buserelin to GnRH receptors by 50%.

Rat Pituitary GnRH Receptor Binding Assay

Crude plasma membranes prepared from rat pituitary tissues were incubated in a Tris.HCl buffer (50 mM, PH. 7.5) containing bovine serum albumin (0.1%), [I- 125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LHI Release Assay

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of $3 \times 10^5$ cells/ml, and 1.0 ml of this suspension was placed in each well of a 24-well tray (Costar, Cambridge, Mass.). Cells were maintained in a humidified 5% $CO_2$-95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1 ½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be usefuil in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89107110, and PCT Patent Pub. No. are WO 89/07111) and GHRP-2 (described in PCT Patent Pub. No. WO 93/04081), as well as hexarelin (J. Endocrinol Invest., 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; Science 260 1640–1643 (Jun. 11, 1993); Ann. Rep. Med. Chem., 28,177–186(1993); Bioorg. Med. Chem. Ltrs., 4(22),2709–2714 (1994); and Proc. Natl. Acad. Sci. USA 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl) ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl) ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl) ethyl]-2-amino-2-methylpropanamide;
4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;
5) N-[1(R)-[(2-Acetyl-1,2,3,4-tetrahydrospiro [isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro1-methanesulfonyl-5-fluorospiro [3H-indole-3,4'-piperidin]-1'-yl)carbonyl]-2-(phenylmethyloxy)ethyl-2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;
11) N-[1(R)-[(1,2-Dihydro-1-methanesulifonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl) methylsulfonylspiro-(3H-indole-3,4'-piperidin]-1'-yl) carbonyl]-2-(1H-indol-3-yl)ethyl]-2-amino-2-methylpropanamide;
17) N-[1(R)-[( 1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat.

No. 4,922,007; U.S. Pat. No. 4,942,157; U.S. Pat. No. 5,227,506; U.S. Pat. No. 5,270,365; EPO Patent Pub. No. 0,252,504; and J. Org. Chem., 36 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSA-MAX®.

Additionally, a compound of the present invention may be co-administered with a 5α-reductase 2 inhibitor, such as finasteride or epristeride; a 5α-reductase 1 inhibitor such as 4,7β-dimethyl-4aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, iand alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic futnction of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

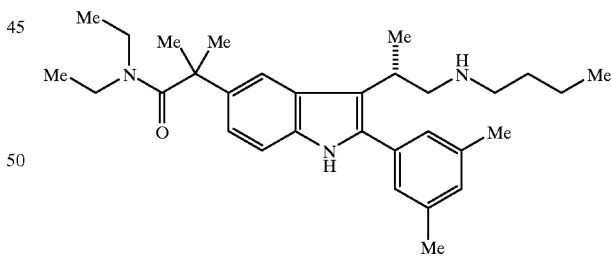

2-[3-(2-butylamino-1-methylethyl)-2-(3,5-dimethylphenyl)-1H-indol-5-yl]-N,N-diethylisobutyramide Step 1A (S)-2-[3-(2-amino-1-methylethyl)-7-bromo-2-(3,5-dimethylphenyl)-1H-indol-5-yl]-2-methylpropionic acid ethyl ester A mixture of 0.107 g of ethyl 2-(3-bromo-4-hydrazinophenyl)-2-methylpropionate, 0.066 g of (R)-4-chloro-1-(3,5-dimethylphenyl)-3-methylbutan-1-one, and 2.0 mL of tert-butanol was stirred at reflux under nitrogen for 16 hours. The cooled solution was concentrated in vacuo, and the residue was partitioned between ethyl acetate and a 10% aqueous sodium thiosulfate solution. The organic phase was washed with water and brine, then dried over sodium sulfate, and filtered. The residue from concentration of the filtrate in vacuo was purified by flash chromatography on silica gel (chloroform:methanol:ammonium hydroxide, 95:5:1) to give the title compound (53 mg).

Step 1B (S)-2-[3-(2-amino-1-methylethyl)-2-(3,5-dimethylphenyl)-1H-indol-5-yl]-2-methylpropionic acid ethyl ester To a solution of (S)-2-[3-(2-amino-1-methylethyl)-7-bromo-2-(3,5-dimethylphenyl)-1H-indol-5-yl]-2-methylpropionic acid ethyl ester (79 mg in 1 mL methanol) was added 8 mg of 10% palladium on carbon catalyst. The reaction flask was fitted with a hydrogen balloon, evacuated and recharged with hydrogen (3 times) and stirred at room temperature. After 7 hours the reaction was flushed with nitrogen, filtered over diatomaceous earth, concentrated in vacuo and purified by flash chromatography on silica gel (chloroform:methanol, 92:8) to provide the title compound (68 mg).

Step 1C (S)-2-[3-(2-tert-butoxycarbonylamino-1-methylethyl)-2-(3,5-dimethylphenyl)-1H-indol-5-yl]-2-methylpropionic acid ethyl ester To a solution of (S)-2-[3-(2-amino-1-methylethyl)-2-(3, 5-dimethylphenyl)-1H-indol-5-yl]-2-methylpropionic acid ethyl ester (2.13 g in 30 mL tetrahydrofuran) at 0° C. was added a solution of di-tert-butyl dicarbonate (1.9 g in 6 mL tetrahydrofuran) followed by poatssium carbonate (1.2 g in 5 mL water) and the resulting suspension stirred vigorously at 0° C. After 20 minutes, the reaction was quenched by the addition of excess saturated aqueous ammonium chloride and the mixture extracted with ethyl acetate. The organic portion was dried over sodium sulfate and concentrated in vacuo. The residue was purified by flash chromatography on silica gel (hexane:methylene chloride:ethyl acetate, 7.5:7.5:1) to give the title compound (2.52 g).

Step 1D (S)-2-[3-(2-tert-butoxycarbonylamino-1-methylethyl)-2-(3,5-dimethylphenyl)-1H-indol-5-yl]-2-methylpropionic acid To a stirred solution of (S)-2-[3-(2-tert-butoxycarbonylamino-1-methylethyl)-2-(3,5-dimethylphenyl)-1H-indol-5-yl]-2-methylpropionic acid ethyl ester (2.5 g in 80 mL methanol) was added 26 mL of 2.0N potassium hydroxide and the mixture heated to 94° C. on an oil bath. After 14 hours the mixture was cooled to 0° C., acidified to pH5 and extracted with ethyl acetate. The organic layer was washed with saturated ammonium chloride, dried over sodium sulfate and concentrated in vacuo to give the crude title compound (2.4 g).

Step 1E (S)-{2-[5-(1-diethylcarbamoyl-1-methylethyl)-2-(3,5-dimethylphenyl)-1H-indol-3-yl]-propyl}-carbamic acid tert-butyl ester To a stirred solution of (S)-2-[3-(2-tert-butoxycarbonylamino-1-methylethyl)-2-(3,5-dimethylphenyl)-1H-indol-5-yl]-2-methylpropionic acid in dry methylene chloride at 0° C. is added 1-hydroxybenzotriazole followed by 1-(3-dimethylaminopropyl)-3-ethylcarbodiimide hydrochloride and the reagents allowed to mix for 1 hour. At this time diethylamine is added followed by 1.5 mL triehtylamine and the reaction stirred at room temperature. After completion, the mixture is concentrated in vacuo and purified by flash chromatography on silica gel to give the title compound.

Step 1F (S)-2-[3-2-amino-1-methylethyl)-2-(3,5-dimethylphenyl)-1H-indol-5-yl]-N,N-diethylisobutyramide To a solution of (S)-{2-[5-(1-diethylcarbamoyl-1-methylethyl)-2-(3,5-dimethylphenyl)-1H-indol-3-yl]-propyl}-carbamic acid tert-butyl ester in dry methylene chloride at 0° C. is added anisole followed by trifluoroacetic acid and the mixture stirred at 0° C. After 2 hours, the mixture is concentrated in vacuo and the residual acid removed by azeotrope with toluene. Purifiaction by flash chromatography on silica gel gives the title compound.

Step 1G (S)-2-[3-(2-butylamino-1-methylethyl)-2-(3,5-dimethylphenyl)-1H-indol-5-yl]-N,N-diethylisobutyramide To a solution of (S)-2-[3-(2-amino-1-methylethyl)-2-(3, 5-dimethylphenyl)-1H-indol-5-yl]-N,N-diethylisobutyramide in dry chloroform at 0° C. is added magnesium sulfate followed by butyraldehyde and the mixture stirred at low temperature. After 30 minutes, a solution of sodium borohydride in methanol is added and the reaction allowed to proceed at 0° C. After completion, the reaction is quenched by the addition of saturated sodium bicarbonate and the mixture extracted with ethyl acetate. The organic portion is washed with saturated aqueous sodium bicarbonate and then dried over sodium sulfate. Purification of the concentrate by flash chromatography on silica gel gives the title compound.

PREPARATION OF SYNTHETIC INTERMEDIATES

Ethyl 2-(3-bromo-4-hydrazinophenyl)-2-methylpropionate

Step A: Ethyl (±)-2-(4-nitrophenyl)propionate

To a solution of 9.76 g (50 mmol) of (±)-2-(4-nitrophenyl) propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-ethyl acetate. 400 MHz $^1$H NMR (CDCl$_3$) was consistent with the assigned structure.

Step B: Ethyl 2-methyl-2-(4-nitrophenyl)propionate

A suspension of 924 mg (23 mmol) of sodium hydride (60% in oil) in 21 mL of dry N,N-dimethylformamide was stirred under nitrogen in an ice bath as a solution of 4.68 g (21 mmol) of ethyl (±)-2-(4-nitrophenyl)propionate in 20.5 mL of dry N,N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of methyl iodide in 5 mL of dry N,N-dimethylformamide was added dropwise by syringe over about 10 minutes, while maintaining the internal temperature at 10°–15° C. The mixture was allowed to warm to room temperature, and the color changed to brown. After 1 hour, an additional 187 mL (426 mg, 3 mmol) of iodomethane was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additonal 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-ethyl acetete) yielded 4.31 g (87%) of an oil; homogeneous by TLC in 9:1 hexane-ethyl acetete. 400 MHz $^1$H NMR (CDCl$_3$) was consistent with the assigned structure.

Step C: Ethyl 2-(4-aminophenyl)-2-methylpropionate

A mixture of 4.27 g (18 mmol) of ethyl 2-methyl-2-(4-nitrophenyl)propionate, 200 mg of 10% palladium on carbon, and 120 mL of absolute ethanol was shaken with hydrogen (initial hydrogen pressure 47 psig) in a pressure vessel for 2 hours. The catalyst was removed by filtration through Celite under nitrogen, and the filter cake was washed with additional ethanol. Concentration of the filtrate in vacuo at up to 50° C. gave 3.74 g (100%) of an oil; homogeneous by TLC in 4:1 hexane-EtOAc. 400 MHz $^1$H NMR (CDCl$_3$) was consistent with the assigned structure. Mass spectrum (ESI): m/e=208 (M+H).

Step D: Ethyl 2-(4-amino-3-bromophenyl)-2-methylpropionate

To a solution of ethyl $^2$-(4-aminophenyl)-2-methylpropionate (4.74 g in 40 mL dry methylene chloride) at 0° C. was added 4.08 g of N-bromosuccinimide and the mixture stirred at low temperature. After 1 hour, the mixture was warmed to room temperature and concentrated in vacuo. Purification of the residue by flash chromatography on silica gel (hexane:ethyl acetate, 9:1; then 8:2) gave the title compound, 5.46 g.

Step E: Ethyl 2-(3-bromo-4-hydrazinophenyl)-2-methylpropionate

A solution of 0.091 g of ethyl 2-(4-amino-3-bromophenyl)- 2-methylpropionate in 0.32 mL of concentrated hydrochloric acid was stirred at −10 to −5° C. in an ice-acetone bath as a solution of 0.023 g of sodium nitrite in 0.20 mL of water was added dropwise over about 15 minutes. Stirring was continued at this temperature for an additional 30 minutes. Next, the supernatant was removed by syringe and added dropwise over 10 minutes to a solution of 0.36 g of stannous chloride dihydrate in 0.25 mL of concentrated hydrochloric acid stirred under nitrogen in an ice-acetone bath. The addition was carried out at such a rate that the internal temperature remained at about −5° C. A gummy material separated during the addition. After completion of the addition, strrring was continued at −10 to −5° C. for 1 hour. The mixture was then diluted with 60 mL ethyl acetate and washed with sodium carbonate. The organic layer was washed with water and brine then dried over magnesium sulfate. Concentration in vacuo gave the crude title compound.

(R)-4-Chloro-1-(3,5-dimethylphenyl)-3-methylbutan-1-one

Step AA: (R)-4-hydroxy-3-methylbutyronitrile

To a solution of (S)-3-bromo2-methyl-propan-1-ol (5.83 g in 25 mL dry N,N-dimethylformamide) was added 9.33g sodium cyanide and the mixture heated to 80° C. on an oil bath. After 4 hours, the mixture was cooled to room temperature, diluted with water and extracted with ethyl acetate. The combined organics were washed with water then brine. Concentration in vacuo gave the desired crude product (2.74 g).

Step BB: (R)-4-methyldihydrofuran-2-one

To a solution of (R)-4-hydroxy-3-methyl-butyronitrile (2.73 g in 39 mL ethanol) was added a solution of sodium hydroxide (1.64 g in 13 mL water) and the mixture heated to reflux on an oil bath. After 7 hours, the mixture was cooled and made acidic by the addition of 2N hydrochloric acid. The organics were removed in vacuo and the mixture then extracted with 90 mL benzene. The organics were washed with brine and transferred to a reaction flask fitted with a Dean-Stark trap. p-Toluenesulfonic acid (100 mg) was added and the mixture heated to reflux on an oil bath. After 3 hours, the benzene and product (138° C.) were collected by distillation under reduced pressure (1.79 g).

Step CC: (R)-3-(3,5-dimethylbenzoyl)-4-methyldihydrofuran-2-one

To a solution of (R)-4-methyldihydrofuran-2-one (1.68 g in 40 mL dioxane) were added 5.51 g 3,5-dimethylbenzoic acid methyl ester followed by 1.82 g sodium hydroxide and the mixture heated to reflux on an oil bath. After 3 hours, the mixture was cooled to room temperature and the pH neutralized by the addition of 0.5N hydrochloric acid. The mixture was then extracted with ethyl acetate and the organic portion washed with brine and diied over sodium sulfate. Purification of the concentrate by flash chromatography on silica gel (hexane:ethyl acetate, 9:1) gave the title compound (2.42 g).

Step DD: (R)-4-chloro-1-(3,5-dimethylphenyl)-3-methylbutan-1-one

To a solution of (R)-3-(3,5-dimethylbenzoyl)-4-methyldihydrofuran-2-one (2.42 g in 15 mL dioxane) was added 15 mL conc. hydrochloric acid and the mixture heated to reflux on an oil bath. After one hour, the reaction was poured into cold, saturated aqueous sodium bicarbonate. Additional solid sodium bicarbonate was added until all acid was neutralized. This was then extracted with ethyl acetate, washed with brine. Concentration in vacuo provided the title compound (2.12 g).

What is claimed is:

1. A compound of the formula

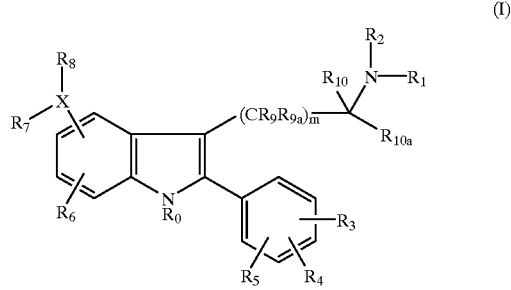

(I)

wherein $R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R_5$;

$R_1$ and $R_2$ are independently hydrogen, $C_1$–$C_6$ alkyl, substituted $C_1$–$C_6$ alkyl, $C_3$–$C_7$ cycloalkyl, substituted $C_3$–$C_7$ cycloalkyl, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$, $C_3$–$C_6$ alkenyl, substituted $C_3$–$C_6$ alkenyl, $C_3$–$C_6$ alkynyl, substituted $C_3$–$C_6$ alkynyl, $C_0$–$C_5$-alkyl-$S(O)_n$—$C_0$–$C_5$ alkyl, $C_2$–$C_6$ alkyl($NR_{11}R_{12}$), $C_2$–$C_6$ alkyl($OR_{11}$), or $C_1$–$C_6$alkyl ($CONR_{11}R_{12}$); with the proviso that $R_{11}$ and $R_{12}$ independently or taken together are not aryl, substituted aryl, aralkyl, or substituted aralkyl; or $R_1$ and $R_2$ taken together form a non-heteroaromatic ring of 3–8 atoms containing 0,1 or 2 additional heteroatoms selected from S, O or N;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, $R_{11}O$ $(CH_2)_p$-, $R_{11}C(O)O(CH_2)_p$-, $R_{11}OC(O)(CH_2)_p$-, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$-, $NR_{12}C(O)R_{11}$, $NR_{12}C(O)NR_{11}R_{12}$ or $SO_nR_{11}$;

$R_7$ is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{20}R_{21}$, N $R_{20}R_{21}$, $C(O)R_{11}$, $NR_{20}C(O)R_{11}$, $NR_{20}C(O)N$ $R_{20}R_{21}$, $NR_{20}S(O)_2R_{11}$, $NR_{20}S(O)_2NR_{20}R_{21}$, $OC(O)R_{11}$, $OC(O)NR_{20}R_{21}$, $OR_{11}$, $SO_nR_{11}$, $S(O)_nNR_{20}R_{21}$, $C_1$–$C_6$ alkyl or substituted $C_1$–$C_6$ alkyl, unless X is hydrogen or halogen, then $R_8$ is absent; or $R_7$ and $R_8$ taken together form a carbocyclic ring of 3–7 atoms;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or $$\overset{O}{\underset{\|}{}}$$

when m,≠0;

$R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or $$\overset{O}{\underset{\|}{}};$$

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{20}$ and $R_{21}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

X is hydrogen, halogen, N, O, $S(O)_n$, $C(O)$, $(CR_{11}R_{12})_p$; $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, S(O)n, C(O), or $CR_{11}R_{12}$ only $R_7$ or $R_8$ is possible;

Z is O, S, or $NR_{11}$;

m is 0–3;

n is 0–2;

p is 0–4; and the alkyl, alkenyl and alkynyl substituents are selected from $C_1$–$C_6$ alkyl, $C_3$–$C_7$ cycloalkyl, hydroxy, oxo, cyano, $C_1$–$C_6$ alkoxy, fluoro, $C(O)OR_{11}$, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

2. The compound according to claim 1 of the formula

3. A pharmaceutical composition which comprises an effective amount of a compound as defined in claim 1 and a pharmaceutically acceptable carrier therefor.

4. A method for antagonizing gonadotropin-releasing hormone in a subject in need thereof which comprises administering to said subject an effective amount of a compound as defined in claim 1 to a subject suffering from a gonadotropin-releasing hormone derived disorder.

5. A method according to claim 4 wherein the gonadotropin-releasing hormone derived disorder is a sex-hormone related condition.

6. A method according to claim 5 wherein the gonadotropin-releasing hormone derived disorder is a sex hormone dependent cancer, benign prostatic hypertropy or myoma of the uterus.

7. A method according to claim 6 wherein the sex hormone dependent cancer is selected from the group consisting of prostatic cancer, uterine cancer, breast cancer and pituitary gonadotrophe adenomas.

8. A method according to claim 5 wherein the sex hormone related condition is selected from the group consisting of endometriosis, polycystic ovarian disease, uterine fibroids and precocious puberty.

9. A method for preventing pregnancy in a subject in need thereof which comprises administering an effective amount of a compound as defined in claim 1.

10. A method for treating lupus erythematosis in a subject in need thereof which comprises administering to said subject an effective amount of a compound as defined in claim 1.

11. A method for treating irritable bowel syndrome in a subject in need thereof which comprises administering to said subject an effective amount of a compound as defined in claim 1.

12. A method for treating p remenstrual syndrome in a subject in need thereof which comprises administering to said subject an effective amount of a compound as defined in claim 1.

13. A method for treating hirsutism in a subject in need thereof which comprises administering to said subject an effective amount of a compound as defined in claim 1.

14. A method for treating short stature or a growth hormone deficiency in a subject in need thereof which comprises administering to said subject an effective amount of a compound which stimulates the endogenous production or release of growth hormone and an effective amount of a compound as defined in claim 1.

15. A method for treating sleep disorders such as sleep pnea in a subject in need thereof which comprises administering to aid subject an effective amount of a compound as defined in claim 1.

16. A pharmaceutical composition which comprises an inert carrier and an effective amount of a compound which stimulates the endogenous production or release of growth hormone in combination with a compound as defined in claim 1.

17. A pharmaceutical composition made by combining the compound of claim 1 and a pharmaceutically acceptable carrier therefor.

18. A process for making a pharmaceutical composition comprising combining a compound of claim 1 and a pharmaceutically acceptable carrier.

19. A method of treating bone loss during treatment with a GnRH antagonist which comprises the co-administration of an effective amount of an estrogen, a progesterone and an androgen and an effective amount of a compound as defined in claim 1.

* * * * *